US011850281B2

United States Patent
Wu

(10) Patent No.: US 11,850,281 B2
(45) Date of Patent: Dec. 26, 2023

(54) REV-DEPENDENT LENTIVIRAL VACCINE PARTICLES FOR REDUCING VIRAL REBOUND AND VIRAL RESERVOIRS IN VIVO

(71) Applicant: Yuntao Wu, Manassas, VA (US)

(72) Inventor: Yuntao Wu, Manassas, VA (US)

(73) Assignee: George Mason Research Foundation, Inc., Fairfax, VA (US)

( * ) Notice: Subject to any disclaimer, the term of this patent is extended or adjusted under 35 U.S.C. 154(b) by 893 days.

(21) Appl. No.: 16/758,577

(22) PCT Filed: Oct. 23, 2018

(86) PCT No.: PCT/US2018/057065
§ 371 (c)(1),
(2) Date: Apr. 23, 2020

(87) PCT Pub. No.: WO2019/083976
PCT Pub. Date: May 2, 2019

(65) Prior Publication Data
US 2020/0345833 A1   Nov. 5, 2020

Related U.S. Application Data

(60) Provisional application No. 62/575,629, filed on Oct. 23, 2017.

(51) Int. Cl.
| | |
|---|---|
| *A61P 31/18* | (2006.01) |
| *A61K 39/02* | (2006.01) |
| *A61K 39/42* | (2006.01) |
| *A61K 45/06* | (2006.01) |
| *A61K 39/00* | (2006.01) |

(52) U.S. Cl.
CPC .............. *A61K 39/02* (2013.01); *A61K 39/42* (2013.01); *A61K 45/06* (2013.01); *A61P 31/18* (2018.01); *A61K 2039/5256* (2013.01); *C12N 2710/16634* (2013.01); *C12N 2710/16671* (2013.01); *C12N 2740/15034* (2013.01); *C12N 2740/15043* (2013.01); *C12N 2740/15071* (2013.01)

(58) Field of Classification Search
None
See application file for complete search history.

(56) References Cited

U.S. PATENT DOCUMENTS

| | | | |
|---|---|---|---|
| 2007/0134767 A1 | 6/2007 | Wu et al. | |
| 2010/0137415 A1 | 6/2010 | Chono et al. | |
| 2011/0104789 A1 | 5/2011 | Wu et al. | |

FOREIGN PATENT DOCUMENTS

WO    2008151633 A2    12/2008

OTHER PUBLICATIONS

Zhirui Wang, et al., "Development of a Non-integrating Rev-dependent Lentiviral Vector Carrying Diphtheria Toxin A Chain and Human TRAF6 to Target HIV Reservoirs," Gene Therapy, Sep. 2010. pp. 1063-1076, vol. 17(9).
Carin K. Ingemarsdotter et al., "Expression of Herpes Simplex Virus Thymidine Kinase/Ganciclovir by RNA Trans-Splicing Induces Selective Killing of HIV-Producing Cells," Molecular Therapy: Nucleic Acids, Jun. 2017. pp. 140-154, vol. 7.
Jessica Young et al., "Selective Killing of HIV-I-positive macrophages and T cells by the Rev-dependent lentivirus carrying anthrolysin O from Bacillus anthracis," Retrovirology, Apr. 2008, pp. 1-15, vol. 5(36).
International Search Report and Written Opinion for PCT/US18/57065, dated Jan. 16, 2019.
Office action for related China Application No. 2018800691928, dated Feb. 24, 2023.

*Primary Examiner* — Michael D Burkhart
(74) *Attorney, Agent, or Firm* — Pilloff Passino & Cosenza LLP; Sean A. Passino; Rachel K. Pilloff

(57) ABSTRACT

Persistence of HIV in anatomic sanctuary sites such as the brain prevents viral eradication. Although combination anti-retroviral therapy (cART) inhibits viral replication to undetectable level by standard clinical assay, it does not selectively eliminate virus reservoirs. To target HIV reservoirs, the present inventor developed an HIV Rev-dependent lentiviral vector carrying a series of therapeutic genes, such as diphtheria toxin, anthrolysin O from *Bacillus anthracis*, human TRAF6, or the herpes simplex 1 virus thymidine kinase gene (HSV-tk). The present disclosure provides the Rev-dependent vectors for targeting viral reservoir in a SIV/rhesus macaque model. SIV-infected rhesus macaques were first treated with cART for over 6 months starting 12 weeks post infection, followed by injections with viral particles assembled from a SIV Rev-dependent vector carrying HSV-tk. Following particle injection, animals were further treated briefly (two weeks) with ganciclovir (GCV), which induces the killing of SIV+, HSV-tk expressing cells. cART was terminated following the GCV treatment, and there was observed a partial control of viral rebound over a period of 4 months after cART cessation. The animal was further treated with additional Rev-dependent vector particles, and viral load was diminished to the undetectable level for over 1 year in the absence of any treatment. These results suggest that the Rev-dependent vector, with or without a functional gene, has the potential to diminish viral reservoirs in vivo and can offer a cure of functional cure of HIV/SIV infection.

7 Claims, 9 Drawing Sheets

FIGURE 7

Figure 1:
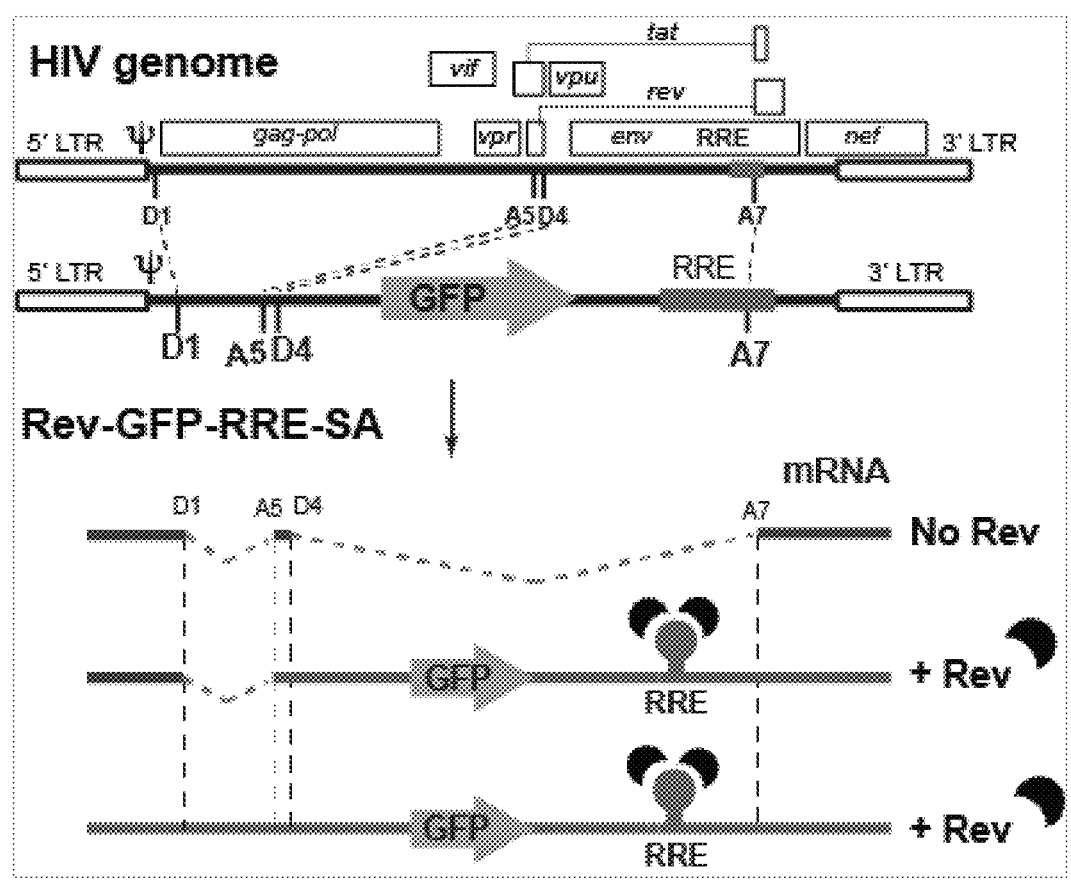

REV-DEPENDENT LENTIVIRAL VACCINE PARTICLES FOR REDUCING VIRAL REBOUND AND VIRAL RESERVOIRS IN VIVO

CROSS-REFERENCE TO RELATED APPLICATION

This application claims priority benefit to U.S. Provisional Application No. 62/575,629, filed Oct. 23, 2017, the content of which application is incorporated herein by reference in its entirety.

STATEMENT REGARDING FEDERALLY SPONSORED RESEARCH

This invention was made with U.S. Government support under grant number R01 MH102144, awarded by the National Institutes of Health. The U.S. Government has certain rights in this invention.

FIELD

The present disclosure embodies compositions, articles, methodology, and the like for treating HIV infection.

INTRODUCTION

Persistence of HIV in anatomic sanctuary sites such as the peripheral blood, lymphoid tissues, and the brain prevents viral eradication. Although combination antiretroviral therapy (cART) inhibits viral replication to undetectable level by standard clinical assay, it does not selectively eliminate virus reservoirs.

The success of cART, marked by a drastic reduction in plasma viremia (1-5), has turned HIV infection from a deadly disease to a manageable chronic infection. However, the persistence of viral reservoirs in the presence of cART precludes a cure (6-13).

The primary viral reservoirs have been proposed to be blood resting CD4 T cells and cells of the monocyte/macrophage lineage (14, 15). Both are the natural targets of HIV-1. Eisele and Siliciano defined viral reservoirs as "an infected cell population that allows the persistence of replication-competent HIV-1 in human patients on optimal HAART regimens on a timescale of years" (15). It has long been recognized that both blood CD4 T cells and macrophages can be infected by HIV (15-17). In highly pathogenic simian immunodeficiency virus/HIV type 1 (SHIV) chimeric virus infection, both CD4 T cells and macrophages have been identified as the principal reservoirs. In particular, macrophages can sustain high virus loads in rhesus macaques after the depletion of CD4+ T cells (18).

It has been well established that viral rebound will always occur with the cessation of cART due to the persistence of viral reservoirs (6-13). For the past 10 to 15 years, the HIV research field has been focusing extensively on blood resting CD4 T cells as a major reservoir and the source of rebounding viruses (14, 15). In addition, emerging evidence suggests that other cell types in tissues may also serve as important viral reservoirs. For example, it has been shown that rebounding plasma viruses do not entirely reflect the genetic pool of the viruses from resting CD4 T cells (19, 20), suggesting the existence of other reservoirs providing rebounding viruses (21-23). On the other hand, it has been demonstrated that low-level ongoing viral production may occur in the body even with concurrent cART (21-23), suggesting that it may be possible for cells in tissues such as the gut and lymph nodes to continue to produce low levels of HIV.

Thus, based on these findings, rebounding viruses may come from HIV reservoirs that allow (a) the persistence of replication-competent HIV, (b) the continuous production of low-level viral particles or viral proteins in human patients on optimal cART regimens. Viral reservoirs may include both "latent reservoirs", such as resting CD4 T cells that harbor replication-competent HIV but produce no viral proteins, and "active reservoirs" that can continuously produce viral particles or viral proteins. Macrophages are known to be metabolically active and to support sustained, ongoing viral production (24). Macrophages have minimal cytopathology in response to HIV infection and can remain viable for viral production for extended periods of time (18, 25). In conclusion, considerable experimental evidence from numerous animal and human studies has demonstrated that both blood CD4 T cells and the tissue macrophage are major viral reservoirs and important sources of rebounding viruses.

SUMMARY

In one aspect, provided herein are method, composition, and the like for reducing SIV/HIV viral rebound and reducing viral reservoirs through a therapeutic vaccine (HIV-like particles) injected into a subject.

For the first time, and as detailed below in an in vivo animal trial, the present inventor made the surprising discovery that a Rev-dependent vector, with or without a functional gene, can cure HIV/SIV infection, and completely eliminate viral rebound. This is so because (1) an Rev-dependent vector expressing a functional gene can deliver a therapeutic toxic protein or a nuclei acid sequence to induce the killing or apoptosis of HIV/SIV+ cells. An empty Rev-dependent vector can also inactivate viral reservoirs through competitive inhibition of HIV/SIV Tat- and Rev-regulated viral gene transcription and viral genome packaging. That a Rev-dependent vector itself could facilitate anti-HIV/SIV immunity to completely block viral rebound in the absence of cART is indeed unexpected and could not have been predicted.

In so doing, the present inventor determined that the killing of HIV+ positive cells involves very complicated schemes of therapeutic strategy, as enumerated below:

(1) First, use an antibody or anti-HIV/SIV to deplete CD8 T cells from the subject's body to ensure no rejection of the therapeutic vaccine by the body's killer T cells (CD8).

(2) The subject needs a break, about 2 weeks break, from anti-HIV therapy (cART) during vaccine particle injection to allow the injected vaccine particles to amplify and replicate.

(3) Following vaccine particle amplification, anti-HIV therapy (cART) needs to be re-initiated again to decrease viral load to a base line. The present inventors discovered during the below animal trial that if anti-HIV therapy (cART) is not re-initiated, the vaccine will not work, as cART can help the vector work by reducing HIV/SIV replication. This was discovered only through the animal trial, and cannot be predicted.

(4) The present inventors also discovered in the below described animal trial that about 2 weeks or longer of ganciclovir treatment can decrease viral load.

(5) The expression of a therapeutic gene such as HSV-1 TK (thymidine kinase) or TRAF6 in SIV+/HIV+ cells can decrease viral rebound in vivo. This was not known before the present animal trial.

(6) The delivery of Herpes Simplex Virus (HSV) thymidine kinase gene into an HIV/SIV-infected cell can convert the HIV+ cells to cells resembling the "HSV-infected cells in vivo. These cells can be reduced by using anti-HSV drugs such as ganciclovir.

(7) The Rev-dependent vector itself can also reduce viral loads and rebound even without the expression of a functional gene. This was not known before the present animal trial.

In one aspect, provided is a composition for reducing SIV/HIV viral rebound and reducing viral reservoirs in a subject. In one embodiment, the composition is a therapeutic vaccine (HIV-like particles). In another embodiment, the composition comprises a Rev-dependent vector. In another embodiment, the Rev-dependent vector comprises a therapeutic gene, such as HSV-1 TK (thymidine kinase) or TRAF 6 (tumor necrosis factor). In another embodiment, the Rev-dependent vector is an empty Rev-dependent vector that does not express a therapeutic gene. In one embodiment, and as used herein, the subject is a patient, such as a human patient, or an animal.

In another aspect, there is provided a method for reducing SIV/HIV viral rebound and reducing viral reservoirs in a subject, comprising administering to the subject a composition comprising a gene that can either initiate anti-HIV responses or induce the killing of HIV+ cells. In one embodiment, the composition comprises a Rev-dependent vector.

In another aspect, there is provided a method for reducing SIV/HIV viral rebound and inactivating viral reservoirs in a subject, comprising administering to the subject a composition comprising a Rev-dependent vector expressing a gene or express no genes. The vector can inactivate viral reservoirs through competitive inhibition of HIV transcription and viral genome packaging.

In another aspect, provided herein is a Rev-dependent vector system for selective killing of HIV infected cells in a subject, wherein the vector comprises herpes simplex virus thymidine kinase gene (HSV-tk).

In another aspect, the application provides a Rev-dependent vector system for selective killing of HIVinfected cells in a subject, wherein the vector comprises tumor necrosis factor (TRAF6).

In another aspect, provided herein is a method for reducing SIV/HIV viral rebound and reducing viral reservoirs in a subject, comprising administering to the subject a Rev-dependent vector system comprising herpes simplex virus thymidine kinase gene (HSV-tk).

In another aspect, provided herein is a method for reducing SIV/HIV viral rebound and reducing viral reservoirs in a subject, comprising administering to the subject a Rev-dependent vector system comprising tumor necrosis factor (TRAF6).

In another aspect, provided herein is a method for reducing SIV/HIV viral rebound and reducing viral reservoirs in a subject, comprising administering to the subject a Rev-dependent vector system that does not express any gene.

In another aspect, provided is a method for killing of HIV+ positive cells to a subject in need thereof, comprising: (a) administering an antibody or anti-HIV/SIV to deplete CD8 T cells from the subject's body to ensure no rejection of the therapeutic vaccine by the body's killer T cells (CD8); (b) injecting a HIV vaccine particle comprising a Rev-dependent vector system for selective killing of HIVinfected cells; (c) ceasing anti-HIV therapy (cART) during vaccine particle injection for a period sufficient to allow the injected vaccine particles to amplify and replicate, without an anti-HIV/SIV drug blocking the particle's infection of the cells; and (d) following vaccine particle amplification, anti-HIV therapy (cART) is re-initiated again to decrease viral load to a base line. Of course, one of ordinary skill in the art will understand that depending on the type of anti-HIV drug, complete cART cessation may not be necessary, and a cART tapering may suffice. For example, and in one embodiment, when the anti-HIV drug is a reverse transcriptase inhibitor, the drug will block Rev-dependent particle infection of the cells. In other embodiments, when the anti-HIV drug is a protease inhibitor or viral assembly inhibitor, these anti-HIV drugs may not inhibit cell infection and thus cART tapering may suffice.

In one embodiment the period sufficient is 1, 2, 3, 4, 5, 6, 7, 8, 9, 10, 11, 12, 13, 14, 15, 16, 17, 18, 19, 20 days, or preferably, about two weeks, when the viral load is reduced to undetectable levels again. In another embodiment, the time sufficient to reduce plasma viremia is sufficient to reduce to less than 1, 2, 3, 4, or 5%. In another embodiment, the method further comprises administering a cytokine such as IL-2 and INF-y, a HDAC inhibitors such as valproic acid or vorinostat; a chemotherapy drug such as fludarabine; a hybrid CD4-toxin that binds to the viral envelope; or an HIV LTR-based lentiviral vector capable of expressing HSV1-tk.

In another aspect, provided is a method of decreasing viral rebound, comprising: administering to a patient in need of treatment for HIV-1 a regimen of HAART for a period of time sufficient to reduce plasma viremia in the patient; thereafter suppressing the regimen and during the suppression period administering a REV dependent lentiviral vector so as to allow sufficient replication of REV dependent lentiviral in the HIV-1 infected cells; and thereafter administering the patient a second regimen of HAART. In one embodiment, the time sufficient to reduce plasma viremia is sufficient to reduce to less than 1, 2, 3, 4, or 5%. In another embodiment, the method further comprises administering a cytokine such as IL-2 and INF-y, a HDAC inhibitors such as valproic acid or vorinostat; a chemotherapy drug such as fludarabine; a hybrid CD4-toxin that binds to the viral envelope; or an HIV LTR-based lentiviral vector capable of expressing HSV1-tk. In another embodiment, the regimen includes administering one or more antivirals chosen from Tenofovir, Emtriva, and Norvir.

In another aspect, provided is a vaccine comprising, in a pharmaceutically acceptable medium, a Rev-dependent vector comprising a herpes simplex virus thymidine kinase gene (HSV-tk) or no gene (empty Rev-dependent vector).

In another aspect, provided is a therapeutic composition comprising, in a pharmaceutically acceptable medium, a Rev-dependent vector comprising a tumor necrosis factor (TRAF6) or no gene (empty Rev-dependent vector).

Finally, provided is a method for inhibiting HIV/SIV transcription in a subject, comprising administering to the subject a Rev-dependent vector system that does not express any functional gene. As explained above, in some embodiments the subject is a patient, such as a human patient, or an animal.

BRIEF DESCRIPTION OF THE DRAWINGS

FIG. 1 illustrates Rev-dependent vector, REV-GFP-RRE-SA. Shown are the packaging signal (Ψ), RRE, and the splicing donors (D1, D4) and acceptors (A5, A7) and their involvement in splicing. In the absence of HIV Rev, all transcripts are spliced and the GFP ORF is removed, no GFP expression. In the presence of Rev, Rev binds to RRE, preventing splicing, and mediating the nuclear export and translation of the unspliced and singly-spliced GFP-containing mRNAs. GFP is expressed.

Figure 2:
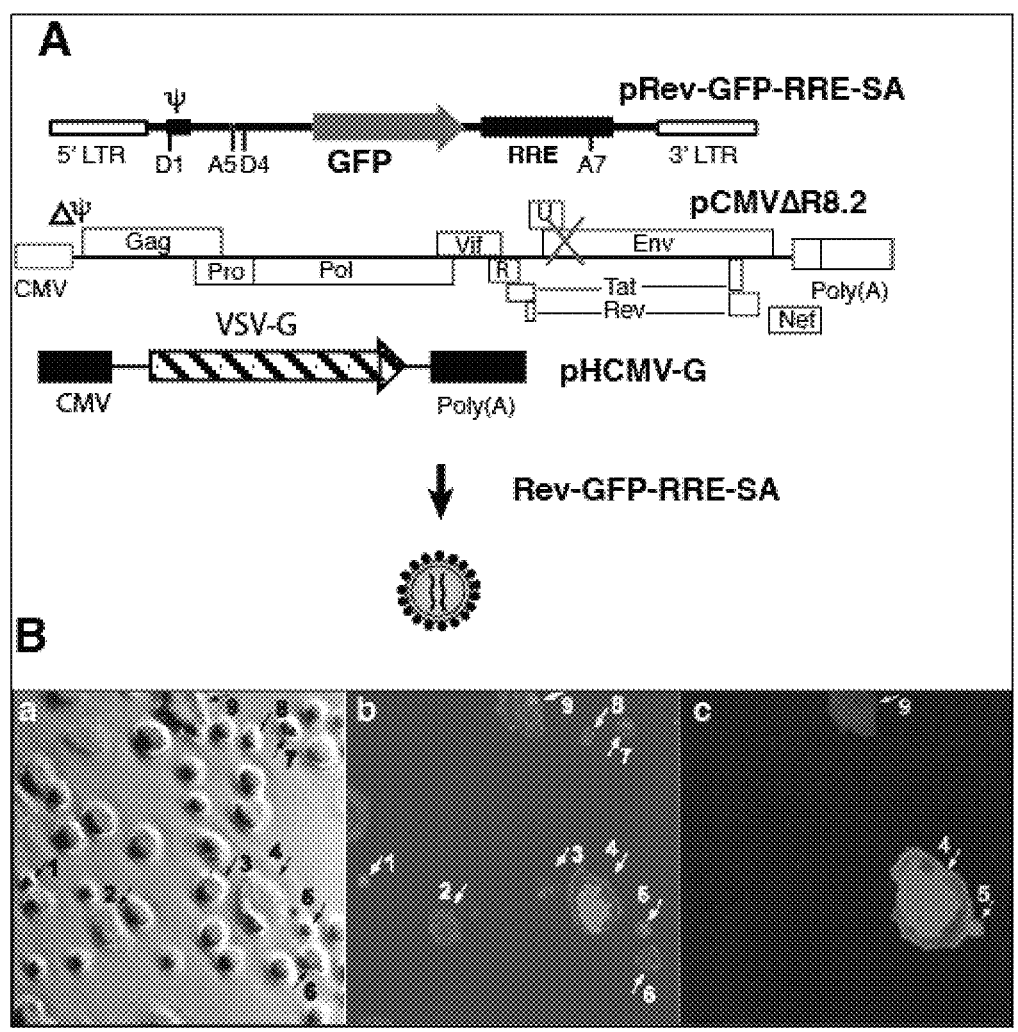

FIG. 2 shows assembly of the Rev-dependent virion particles for identification of HIV-infected macrophages. (A) Viral particles were assembled by cotransfecting of HEK293T cells with the three plasmids, pRev-GFP-RRE-SA; pCMVAR8.2, and pHCMV-G. (B) Tracking HIV-infected macrophages with a Rev-dependent GFP reporter virus. Blood monocyte-derived macrophages were infected with HIVAD8, followed by super-infection with vNL-GFP-RRE-SA. (a) Light microscopy of infected macrophages. (b) The same cells were stained for HIV-1 p24 with a PE-labeled antibody (red fluorescent). (c) The same field is also observed for GFP.

Figure 3:
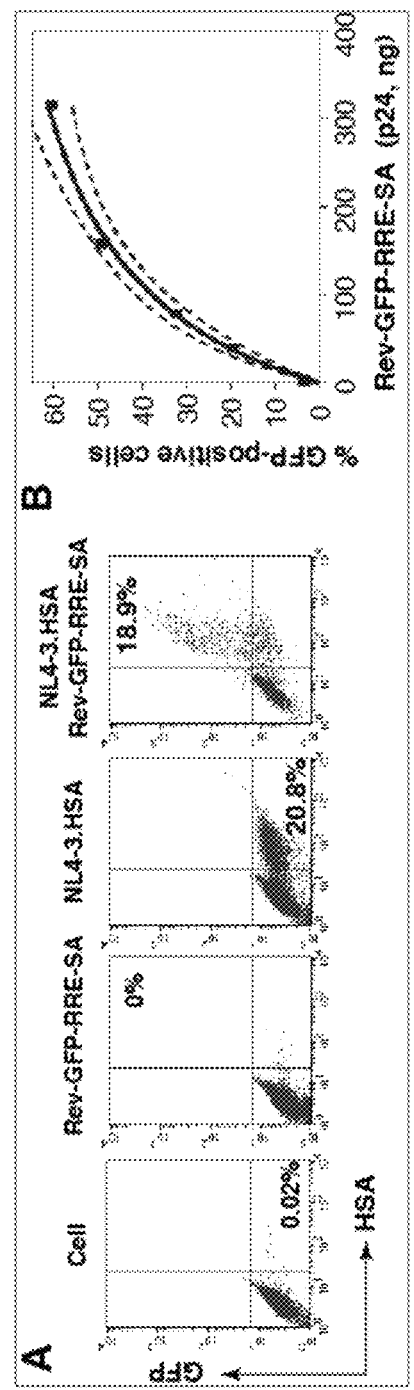

FIG. 3 shows the high specificity of the Rev-dependent vector in mediating HIV-dependent gene expression. (A) CEM-SS cells were not infected or infected with HIV-1 (NL4-3.HSA), followed by super-infection with Rev-GFP-RRE-SA at 24 h. For comparison, cells were also singly infected with either Rev-GFP-RRE-SA or with HIV-1(NL4-3.HSA). Both HSA and GFP expression were analyzed at 72 h. (B) HIV-infected cells (HSA$^+$) were super-infected with varied dosages of Rev-GFP-RRE-SA (x-axis). Flow cytometry yielded percent HIV-positive cells that became GFP-positive after 3 days (y-axis). Non-linear curve fitting (rectangular hyperbola) yielded $R^2$=99.4; maximum GFP-positive=86.1±6.3% (best-fit values ±standard error); $K_D$=128.1±21.5 ng p24. Dashed lines are 95% confidence bands.

Figure 4:
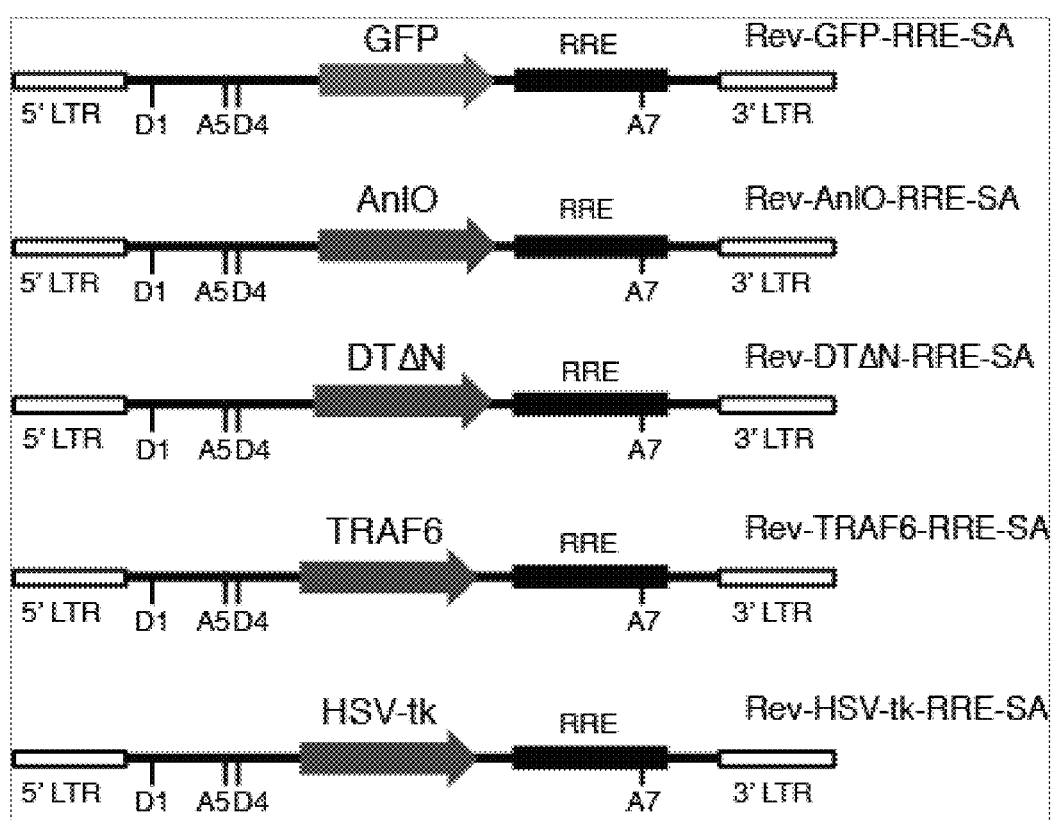

FIG. 4 provides a schematic of the Rev-dependent vectors carrying AnlO, DT-A, TRAF6, and HSV1-tk.

Figure 5:
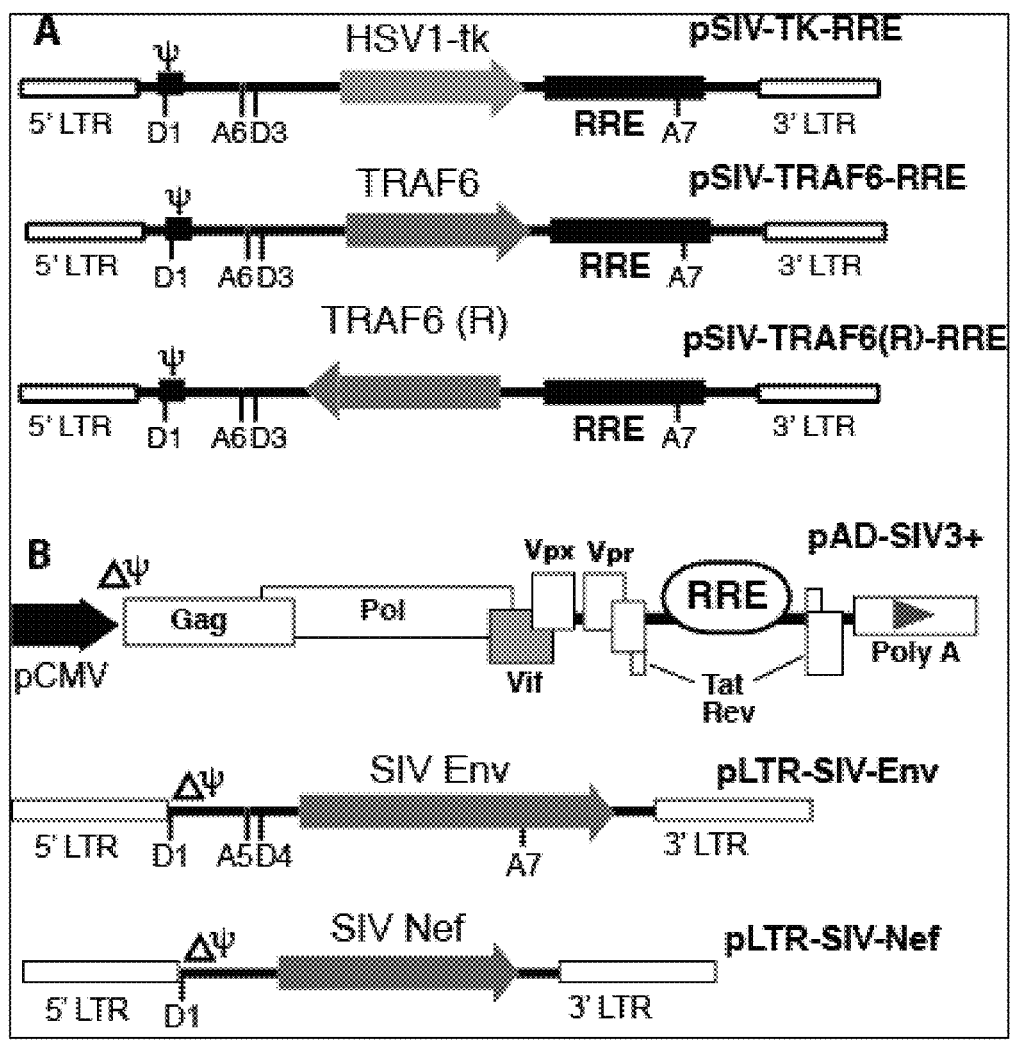

FIG. 5 shows development of the SIV Rev-dependent vectors to target SIV reservoirs. (A) The SIV Rev-dependent vectors carrying therapeutic genes (HSV1-tk or TRAF6) were constructed based on SIVmac239. The structure of these SIV vectors is similar to the HIV Rev-dependent vector. Shown are the packaging signal (Ψ), RRE, and the splicing donors (D1, D3) and acceptors (A6, A7). For TRAF6(R), TRAF6 was placed in the opposite orientation. (B) The helper plasmid, pAD-SIV3+. This plasmid does not contain the viral envelope gene and the nef gene. Both were provided by Env and Nef-expression vectors (pLTR-SIV-Env and pLTR-SIV-Nef). To assemble the virion particle, the SIV Rev-dependent vector, pSIV-HSV-1-tk-RRE, pSIV-TRAF6-RRE or pSIV-TRAF6(R)-RRE, was cotransfected with pAD-SIV3+ plus pLTR-SIV-Env and pLTR-SIV-Nef into HEK293T cells. Viruses were harvested at 48 and 72 h post cotransfection and concentrated for animal injection.

Figure 6:
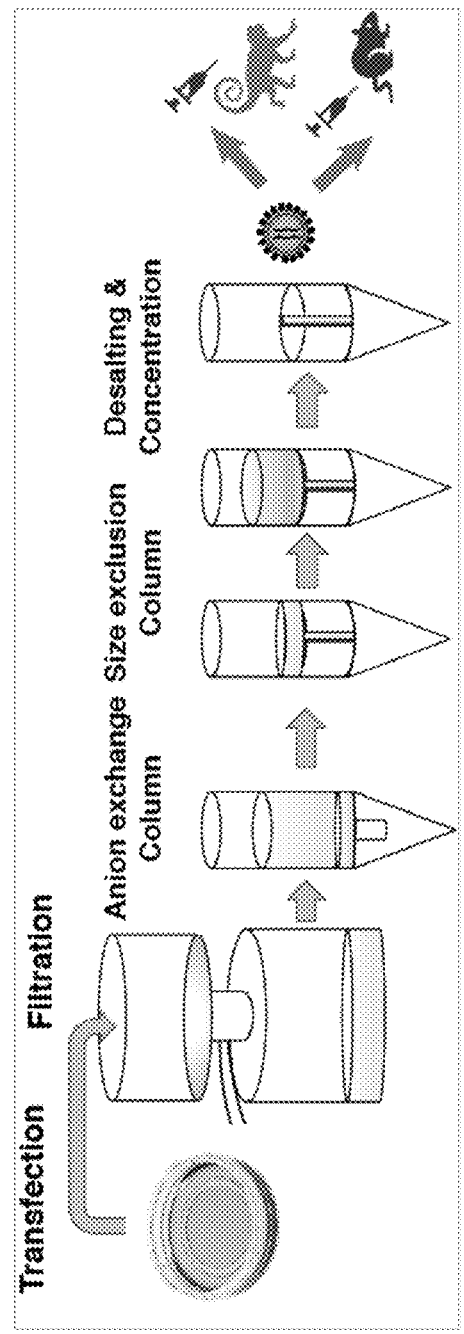

FIG. 6 provides a schematic of Rev-dependent vector assembly, purification, and concentration. Concentrated (500- to 1000-fold) particles were used to inject (i.v.) mice and rhesus macaques to evaluate toxicity.

Figure 7:
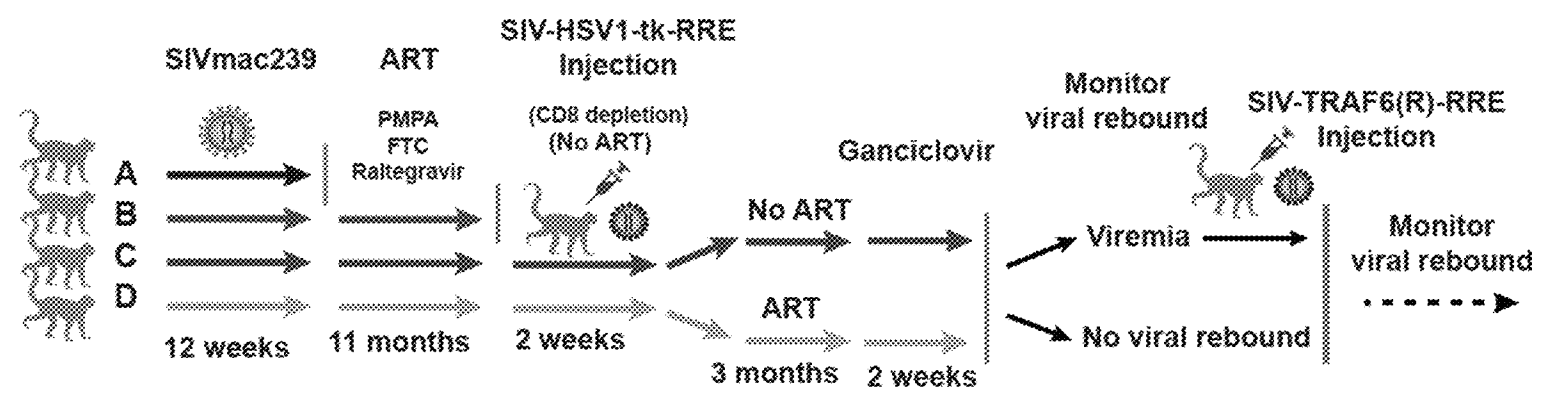

FIG. 7 presents a schematic of the different treatment and vector injection designs for study group A to D.

Figure 8:
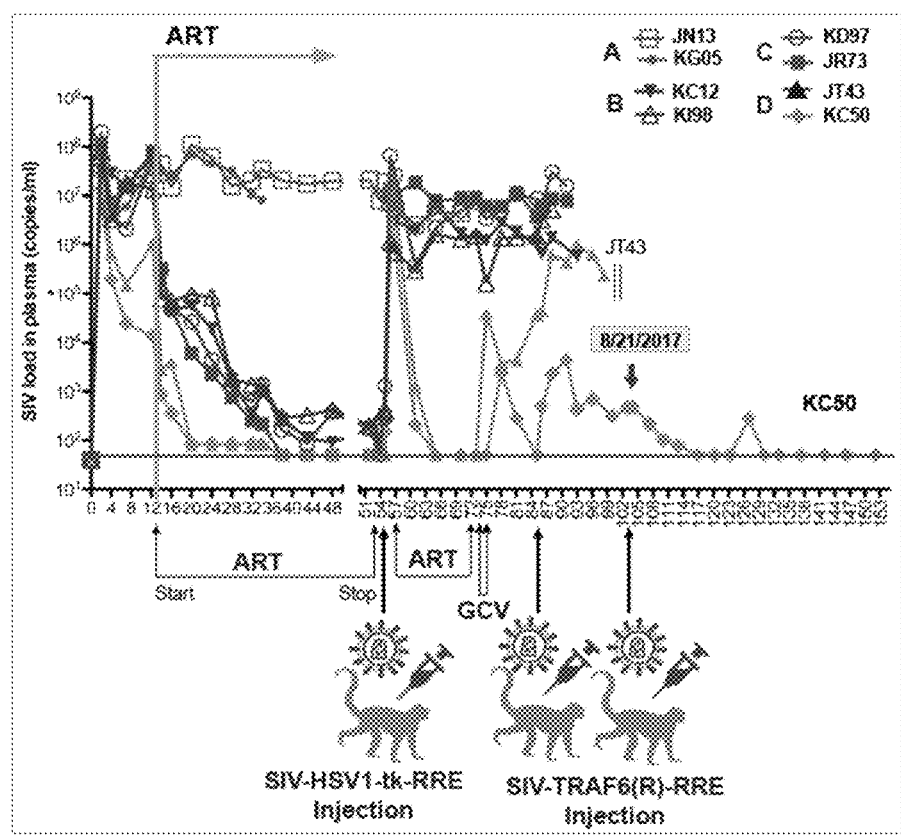

FIG. 8 provides a summary of the results from the animal trial of the Rev-dependent vector, following the schematic of the different treatment and vector injection described in FIG. 7. Y axis is plasma viral load (copies/ml); X axis is time in weeks post SIV infection.

Figure 9:
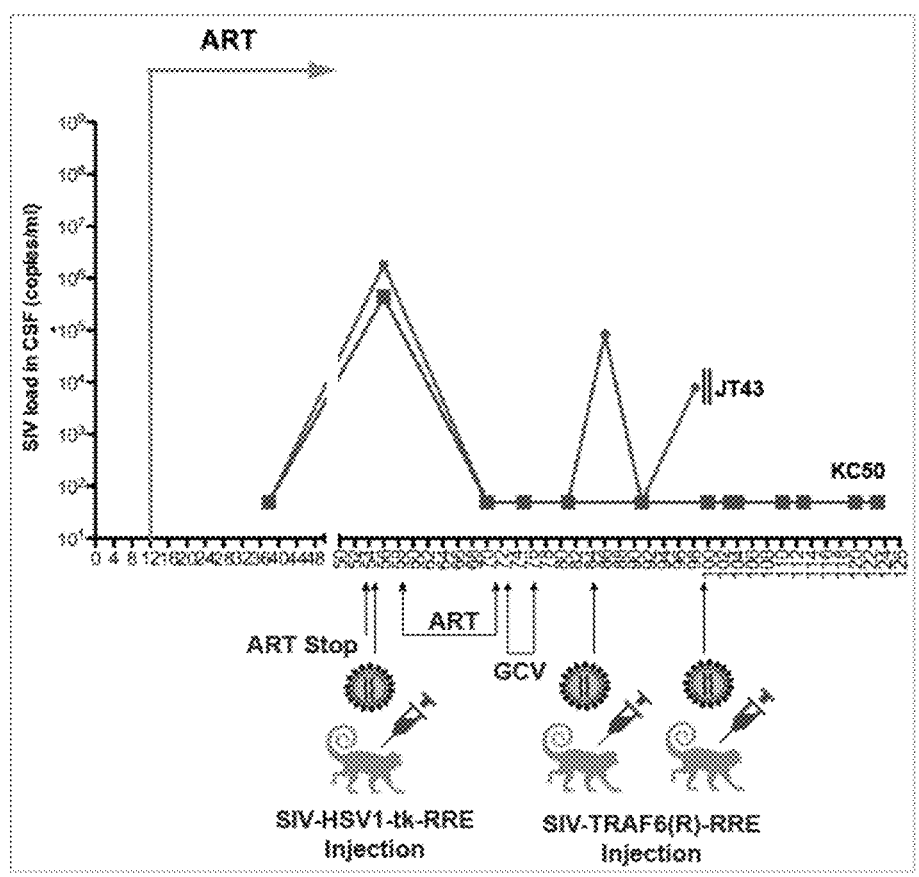

FIG. 9 shows quantification of CSF viral loads in animals treated with the Rev-dependent vector (Group D). Y axis is viral load in CSF (copies/ml); X axis is time in weeks.

DETAILED DESCRIPTION

The persistence of HIV reservoirs remains the most significant obstacle to viral eradication. In particular, cells from the monocyte/macrophage lineages resist HIV-mediated killing and support sustained viral production. Infected macrophages can also infiltrate into the brain and create persistent sites of viral production that elicit pathophysiological consequences, including HIV-Associated Neurocognitive Disorders (HAND). No current antiretroviral therapy (ART) is capable of targeting and eliminating HIV reservoirs in the CNS. As explained below, the present inventor developed a new strategy of targeting and killing these long-lived viral reservoirs.

Recent clinical and experimental attempts to target HIV reservoirs have been largely focused on the "shock and kill" strategy (26-35). A major scientific rationale for this approach is the assumption that viral reservoirs exist mainly in the form of latently infected resting CD4 T cells that do not express any viral genes (14, 15, 36, 37). Thus, these cells may be treated with drugs to activate viral gene expression, which could lead to the killing of the reservoir cells either by the activated HIV itself or by the human immune system. For example, infected patients have been treated with cART plus cytokines such as IL-2 and INF-□ (26-29), HDAC inhibitors such as valproic acid or vorinostat (30, 31, 34, 38), or a chemotherapy drug, fludarabine (39-41), in hopes of purging the latent reservoirs. However, it may be difficult to activate all of the latently-infected cells, given the complexity of HIV latency in different cell subtypes and tissues. In addition, it is not known whether "shocking" can always result in the death of infected cells (30-34).

Alternative approaches to targeting HIV reservoirs have also been tested. For example, HIV-infected cells have been targeted with hybrid CD4 toxins that can bind to the viral envelope displayed on the surface of infected cells (42). In addition, several other studies have explored the popular CRISPR-Cas9 gene editing technique to target viral reservoirs (43-48). This method is simple and efficient in tissue culture conditions. However, it was found that HIV can quickly develop mutations that resist editing by Cas9. The issue may be surmounted by inactivating multiple viral genes at once, or using CRISPR in combination with other anti-HIV drugs. Indeed, with further improvements, a recent study has tested a rAAV vector for delivering multiplex CRISPR-Cas9 to target multiple HIV genes in a humanized mouse model. The study has generated exciting results, demonstrating the possibility of completely inactivating viral reservoirs in vivo (49).

Over the past 15 years, the present inventor has developed an HIV Rev-dependent lentiviral vector for selective targeting of HIV reservoirs (50-54). The Rev-dependent lentiviral vector expresses therapeutic genes under the control of the HIV Rev protein present only in infected cells, thereby, conferring high specificity. In cell culture conditions, the Rev-dependent vector can selectively kill HIV-positive cells, while leaving uninfected cells unharmed (52, 53). See, e.g., U.S. 2007-0134767, published Jun. 14, 2007.

Based on these in vitro results, the present inventor recently conducted the first animal trial of the Rev-dependent vector in the SIV/rhesus macaque model. The results demonstrated that the Rev-dependent vector can effectively diminish SIV rebound with cART cessation; in one of the treated animals, the plasma viral loads were diminished to the threshold of detection. The animal has been controlling viral loads to the undetectable level since the termination of all therapeutic treatment over 12 months ago.

For the first time, and as detailed below in an in vivo animal trial, the present inventor made the surprising discovery that a Rev-dependent vector, with or without a functional gene, can cure HIV/SIV infection, and completely eliminate viral rebound. This is so because (1) an Rev-dependent vector expressing a functional gene can deliver a therapeutic toxic protein or a nuclei acid sequence to induce the killing or apoptosis of HIV/SIV+ cells. An empty Rev-dependent vector can also inactivate viral reservoirs through competitive inhibition of HIV/SIV Tat- and Rev-regulated viral gene transcription and viral genome packaging. That a Rev-dependent vector itself could facilitate anti-HIV/SIV immunity to completely block viral rebound in the absence of cART is indeed unexpected and could not have been predicted.

These results suggest that the Rev-dependent vector has the potential to diminish viral reservoirs in vivo, achieve long-lasting HIV remission, and can offer a functional cure of HIV/SIV infection.

A. Definitions

Viral reservoirs refers to an infected cell population that allows (a) the persistence of replication-competent HIV-1, (b) the continuous production of viral particle or viral proteins in patients on optimal HAART regimens. Viral reservoirs may include "latent reservoirs" such as resting CD4 T cells that harbor replication-competent HIV but produce no viral particles or viral proteins. Viral reservoirs may also include "active reservoirs" such as infected-macrophages that can continuously produce viral particles or viral proteins. It has been known that macrophages are metabolically active and support sustained, ongoing viral production (41). Macrophages have minimal cytopathology in response to HIV infection and can remain viable for viral production for extended periods of time (2, 42).

Viral reactivation means that latent viral reservoirs can be induced to produce viruses or viral proteins either through immunological stimulation (e.g cytokine stimulation (43) or CD3/CD28 activation of resting T cells) or through drug-mediated activation (e. g. vorinostat (18)).

Viral replication means new cycles of infection in which previously uninfected cells become infected and produce infectious viruses which go on to infect additional cells (33).

Viral production refers to viruses produced from previously infected cells, but there may not be new infection of cells from released viruses.

Based on the definitions above, the Rev-dependent vector is capable of targeting "active and latent reservoirs" and "viral reactivation" and can diminish "viral production" or "viral replication".

HIV-like particle refers to an assembled Rev-dependent vector that is capable of stimulating immunity, and thus behaves as a therapeutic vaccine.

Empty vector refers to a Rev-dependent vector that contains LTR and RRE but does not express a functional therapeutic gene, such as TRAF6, for targeting $SIV^{+}$ cells, yet still can decrease viral rebound in vivo. This is so because the empty vector can inhibit HIV replication through several means, such as (1) competitive inhibition of HIV transcription, splicing, and nuclear export; (2) competitive inhibition of HIV genome packaging; (3) protection of uninfected cells from being infected; and (4) stimulation of anti-HIV immunity. Thus, an empty vector competes with HIV for viral proteins and packaging; the empty vector itself may stimulate immunity; and the empty vector can protect uninfected cells.

Rev is an essential viral early protein in the life cycle of HIV. Rev regulates HIV mRNA splicing, nuclear export, and genome packaging through binding to the Rev Response Element (RRE) present in the unspliced and partially-spliced viral mRNAs. The Rev-dependent lentiviral vector, also referred to as Rev-dependent vector system herein, relies on Rev-RRE interaction to regulate gene expression, permitting selective expression of therapeutic genes only in HIV+ cells.

B. HIV Rev-Dependent Lentiviral Vector

As explained below, the present inventors tested a series of therapeutic genes, such as diphtheria toxin, anthrolysin 0 from *Bacillus anthracis*, human TRAF6, or the herpes simplex virus thymidine kinase gene (HSV-tk), in the Rev-dependent vector system for selective killing of HIV infected cells in vitro. In the below described animal trial, HSV-tk and tumor necrosis factor (TRAF6) were used as the therapeutic genes to target SIV+ cells in vivo. HSV-tk phosphorylates ganciclovoir to cause apoptosis through competitive inhibition of dGTP incorporation for DNA synthesis (Tomicic 2002). It is expected that treatment of SIV-infected rhesus macaques with ganciclovoir will kill SIV+ cells, thus reducing viral reservoirs. The second gene, TRAF6, is a TNF receptor associated factor that regulates the NF-kappa B pathway. Overexpression of TRAF6 has been shown to trigger cell apoptosis (He, 2006).

HIV Rev is a virus-encoded early protein that is essential for viral replication. Rev regulates the nuclear export of the non-spliced and singly-spliced viral mRNAs (60, 61) and is required for the translation of viral structural proteins such as Gag and Env (62-64). Rev binds directly to a regulatory element, the Rev-responsive element (RRE), on the unspliced and singly-spliced viral mRNAs (60). This Rev-RRE interaction is required for viral mRNA nuclear export (60) and polysomal association for protein translation (64). The Rev-RRE interaction may also affect viral genomic RNA dimerization for packaging (65-67).

The well-established viral requirement for Rev has led the present inventor to use the Rev-RRE interaction as a regulator to achieve selective expression of therapeutic genes only in HIV infected cells. To do so, the present inventor constructed a HIV Rev-dependent vector, in which a therapeutic or reporter gene is placed before RRE and between the multiple splicing sites (D1, A5, D4, A7) (FIG. 1). This arrangement regulates the therapeutic or reporter gene as a late gene, similar to Gag or Env, and renders its expression fully dependent on Rev. The Rev-dependent vector also contains the viral genomic RNA packaging signal (Ψ). Thus, when cotransfected with HIV assembly helper vectors, it will be packaged into virion particles as the genomic RNA (50).

As shown in FIG. 2A, an HIV Rev-dependent GFP vector was assembled into virion particles (FIG. 2A), and then the particles were used to transduce both human blood monocyte-derived macrophages (MDM) and CD4 T cells, in the absence or presence of HIV (50). The Rev-dependent vector has demonstrated a remarkable capacity to identify HIV+ macrophage and T cells with a high specificity.

C. HIV Rev-Dependent Lentiviral Vectors Express Therapeutic Genes Under the Control of the HIV Tat and Rev Proteins The instant Rev-dependent lentiviral vectors express therapeutic genes under the control of the HIV Tat and Rev proteins, conferring remarkable specificity. They demonstrated that in cell culture conditions, the Rev-dependent vector can selectively kill HIV-positive macrophages, while leaving uninfected cells unharmed. Based on these in vitro results, and as described below, the present inventors provide in vivo therapeutic efficacy of these vectors in SIV/rhesus macaque model.

The present disclosure provides the first animal trial data showing that SIV/HIV viral rebound and viral reservoirs can be reduced through a therapeutic vaccine (HIV like particles) injected into a subject. As explained below, the instant HIV-like therapeutic vaccine particles can be injected into the subject and enter into cells to express genes that can either initiate anti-HIV responses or induce the killing of HIV+ cells.

The disclosure also provides use of an anti-Herpes drug ganciclovir to treat HIV infection by induce the killing of HIV+ cells. This is made possible by using the expression of Herpes simplex virus (HSV) thymidine kinase (HSV-tK) in HIV+ cells to covert the HIV+ cells into cells resembling Herpes simplex virus-infected cells.

In so doing, the present inventor determined that the killing of HIV+ positive cells involve a very complicated schemes of therapeutic strategy, as enumerated below:

(1) First, use an antibody to deplete CD8 T cells from the subject's body to ensure no rejection of the therapeutic vaccine by the body's killer T cells (CD8).

(2) The subject needs a break, about 2 weeks break, from anti-HIV therapy (cART) during vaccine particle injection to allow the injected vaccine particles to amplify and replication.

(3) Following vaccine particle amplification, anti-HIV therapy (cART) is re-initiated again to decrease viral load to a base line. The present inventor discovered during the below animal trial that if anti-HIV therapy(cART) is not re-initiated, the vaccine will not work. This was discovered only through the animal trial, and cannot be predicted.

(4) The present inventor also discovered in the below described animal trial that 2 weeks of gancicloveir treatment can decrease viral load.

(5) The expression of TRAF6 in SIV+/HIV+ cells can decrease viral rebound. This was not known before the present animal trial.

(6) Finally, the TRAF6 vaccine particle does not need to deplete CD8 T cells. This is a surprise and contrasts with the HSV-tK vector that needs the depletion of CD8 T cells before injection.

In the course of constructing the instant Rev-dependent vectors, and as detailed below, the present inventor made the surprising discovery that a Rev-dependent vector, with or without a functional gene, can cure HIV/SIV infection, and completely eliminate viral rebound. This is so because (1) an Rev-dependent vector expressing a functional gene can deliver a therapeutic toxic protein or a nuclei acid sequence to induce the killing or apoptosis of HIV/SIV+ cells. An empty Rev-dependent vector can also inactivate viral reservoirs through competitive inhibition of HIV/SIV Tat- and Rev-regulated viral gene transcription and viral genome packaging. That a Rev-dependent vector itself could facilitate anti-HIV/SIV immunity to completely block viral rebound in the absence of cART is indeed unexpected and could not have been predicted.

D. Methodology (1) Development of SIV-Based Rev-Dependent Vectors for In Vivo Study in Rhesus Macaques As explained below, the present inventor tested the Rev-dependent vector for targeting SIV infection of macaques. For this purpose, all HIV-based vectors were converted into SIV-based vectors by incorporation of multiple splicing sites (D1, A6, D3, A7), RRE, and Loop A (Ψ) from the SIVmac239 genome. The HSV1-tk gene was cloned into the SIV-based vector (FIG. 5). SIV also encodes the Rev protein and the Rev function is well-conserved among HIV and SIV strains. It has been shown that SIV Rev is capable of inducing cytoplasmic expression of incompletely spliced mRNAs (108), and that the Rev proteins of HIV-1 and HIV-2 can also transactivate SIV gene expression (109). In addition, human TRAF6 is identical to monkey TRAF6.

To assemble viral particles, the present inventor acquired an SIV-based helper plasmid, pAD-SIV3+ (110, 111), as well as the non-integrating version of the same vector, pAD-D64V (112, 113). In addition, SIVmac239 nef and gp160 were cloned into an LTR-based expression vector (pLTR-SIV-Nef and pLTR-SIV-Env, data not shown). The envelope protein of SIV uses CCR5 as a co-receptor for entry. Thus, the assembled Rev-dependent viral particle will preferentially infect macrophages and certain CCR5+ T cells such as the activated memory CD4 T cells. These plasmids were cotransfected into HEK293T cells to assemble into virion particles for injection into animals (FIG. 5B).

(2) Targeting SIV Reservoirs with a Rev-Dependent HSV1-Tk Vector

HIV enters the CNS mainly through infected monocytes/macrophages from the periphery (1-3, 44-48). For effective CNS targeting, this major source of viral influx has to be stopped. The present inventor's preliminary studies demonstrated that the Rev-dependent vector can effectively kill HIV-infected cells in vitro (6, 7). Based on these encouraging results, the inventor sought to test the ability of the SIV Rev-dependent vectors to target SIV infection, diminishing active viral production, both in the periphery and in the CNS. For this purpose, the cloned HSV1-tk was used as the therapeutic gene (FIG. 1), based on several advantages of the HSV1-tk system, including:

(a) Superior safety profiles: In comparison with the killing of cells by toxins, the nucleoside analogue/HSV-tk-mediated cell killing has been studied in vitro and in vivo for over thirty years (114-118). This system has also undergone several clinical trials, exhibiting desirable safety and efficacy required for killing of numerous cell types (118-120). Notably, even at high concentrations of HSV-tk vector, $>10^{10}$ transduction units per injection, few side effects were observed (119, 120), suggesting that the Rev-dependent HSV1-tk vector system will be similarly tolerated in this study. Indeed, the HSV-tk system has been adopted for HIV-mediated mobilization and killing of cancer cells (121, 122).

(b) Capable of mobilization and amplification in vivo: In the absence of ganciclovir (GCV), the HSK-tk vector-mediated killing will not occur. Cells can stably harbor the vector and infiltrate into the brain, similar to SIV+ macrophages. The vector also contains fully functional LTR, the packaging signal (Ψ), and RRE, which resemble a previously described conditionally-replicating lentiviral vector that can mobilize in the presence of HIV in infected patients (105). The inventor expected that the SIV-HSV1-tk-RRE vector will amplify following injection into SIV-infected macaques. Macrophages infected with SIV-HSV1-tk-RRE will also infiltrate into the brain and be amplified with SIV replication in the CNS.

(c) Capable of CNS targeting by ganciclovir: GCV has been shown to cross the blood brain barrier (BBB), which will allow CNS-specific targeting of HIV-infected cells (123). Notably, targeted killing of tumor cells in the brain has been observed after HSV-tk vector intrathecal injection and systemic GCV administration in rats (124). These characteristics of the HSV1-tk system suggest that CNS-specific targeting of HIV reservoirs using the Rev-dependent HSV1-tk vector and GCV is viable.

(d) Capable of targeting post-mitotic cells: It has been shown that HIV/SIV infected-brain macrophages have higher levels of DNA metabolism than normal cells. These infected-cells express the proliferating cellular nuclear antigen (PCNA), a marker indicative of SIV-stimulated DNA synthesis and repair activity in these non-proliferating cells (125, 126). This HIV/SIV-stimulated DNA synthesis and DNA repair activity can be utilized for HSV1-tk-mediated killing. A similar approach using HSV1-tk and GCV to kill terminally-differentiated synovial lining cells has been applied in a rabbit inflammatory arthritis model (127). This treatment effectively inhibited inflammation and reduced joint swelling in the HSV-TK-transduced knees.

(e) High titer particles can be assembled: The lack of cytotoxicity of HSV1-tk in the absence of GCV has permitted the production of high titer lentiviral particles. Previous studies have demonstrated that high titer viral particles ($>10^{10}$ transduction units) can be produced and injected into animals (119, 120). This feasibility of producing higher titer viral particles will greatly facilitate the animal study.

(3) CD8-Depletion Model to Accelerate Infection and the CNS Disease.

SW-infected macaques were injected with the SIV-Rev-dependent particles carrying HSV1-tk. Antiretroviral drugs were interrupted to allow vector dissemination and amplification. In the absence of GCV, Rev-mediated HSV1-tk killing of SIV-positive cells will not occur. But SIV-dependent vector mobilization will take place and be maximized in 1-2 weeks (105). It was expected that infected macrophages carrying HSV1-tk will also infiltrate into the brain and be amplified with SIV replication in the CNS.

To further facilitate vector mobilization and amplification, if needed, animals may also be treated with clinical HDAC inhibitors such as vorinostat to stimulate viral replication from latent cells (18). Following vector mobilization, amplification, and cell stimulation, GCV will be administrated intravenously to induce HSV1-tk-mediated killing of SIV-positive cells in the peripheral blood, which is intended to stop the continuous influx of SIV-infected macrophages into the brain. Given that GCV can also enter the CNS from blood plasma, killing of SIV-positive cells in the brain would also occur. The efficacy of this approach was monitored for any significant delay or diminishment of viral rebound upon ART discontinuation. Possible beneficial effects on prevention or delay of SIVE (SIV encephalitis) will also be monitored.

(4) HSV1-Tk Vector Targeting of SIV Infection of Rhesus Macaques.

For this study, a total of 8 Indian rhesus macaques were used which will be divided into 4 groups (2 monkeys in each group, Group A to D). The number of animals used in each group is based on previous experience in animal studies (131, 133, 134). Schemes of treatments are listed in Table 1.

For Group D, monkeys will be infected with 100 TCID50 of SIVmac239 using the standard protocol that we normally use in TNPRC (131, 133, 134). Animals will be treated with cM-T807 to deplete CD8 T cells as described above. Animals will be infected for 6 weeks, and then be treated with ART (Tenofovir, Emtriva, and Norvir) for 6 months. ART will be halted for 3 days, and the SIV-infected monkeys will be intravenously injected with 0.5 ml of highly concentrated ($10^9$-$10^{10}$ Transduction unit/ml) Rev-dependent particles, vSIV-HSV1-tk-RRE. Following vector injection, cM-T807 will be used to further deplete CD8 T cells that are regenerated after 28 days (130). ART will be interrupted for two weeks after vector injection, and then be resumed for 3 months (Table 1). The scheduled ART interruption before lentiviral vector injection is needed for vSIV-HSV1-tk-RRE infection and vector spread in the body. The CD8 depletion and two weeks of ART interruption following vector injection is also needed for vector mobilization which maximizes in 7-10 days (105). The resumption of ART would inhibit uncontrolled SIV spread.

For a comparison, in Group C, animals will be identically infected, treated, and then injected with the vSIV-HSV1-tk-RRE vector as those in Group D, but following vector injection, ART will not be resumed. This will permit higher degree of vector amplification and mobilization with active SIV replication. Animals in Groups D and C will be closely monitored for 3 months following vector injection. At 3 months following vector injection, ganciclovir will be administered intravenously at a dosage of 10 mg/kg/day to induce the death and decay of SIV+ cells. Ganciclovir plasma levels will be maintained by daily i.v. injection for two weeks. Following ganciclovir administration, all treatments will be terminated, and viral rebound will be monitored for an additional 12 months.

For additional controls, Group B will be similarly infected with SIV and treated with ART, but will not be injected with the Rev-dependent particle, vSIV-HSV1-tk-RRE. ART in Group B will be terminated at the end of 6 months to allow viral rebound to occur.

Monkeys in Group A will be infected with SIVmac239 but will not receive any intervention.

Animals in Group A and B are expected to develop AIDS in 4-5 months without ART (130), whereas animals in Groups C and D may experience significant inhibition or delay of viral rebound. These animals may also be free of AIDS and have decreased brain viral burdens and SIV lesions.

TABLE 1

SIV and vSIV-HSV1-tk-RRE injection and treatment scheme

| Group | SIV Infection | ART | vSIV-HSV1-tk-RRE | Post vector injection |
|---|---|---|---|---|
| A = SIV infection only | SIV | NO | NO | N/A |
| B = SIV + ART only | SIV (6 weeks) | 6 months | NO | N/A |
| C = SIV + ART + vSIV-HSV1-tk-RRE | SIV (6 weeks) | 6 months | YES | No ART |

TABLE 1-continued

SIV and vSIV-HSV1-tk-RRE injection and treatment scheme

| Group | SIV Infection | ART | vSIV-HSV1-tk-RRE | Post vector injection |
|---|---|---|---|---|
| D = SIV + ART + vSIV-HSV1-tk-RRE + ART | SIV (6 weeks) | 6 months | YES | ART, 2 weeks off and then 3 months on |

(5) Monitoring the Therapeutic Efficacy of the HSV1-Tk Vector

The therapeutic efficacy of the vSIV-HSV1-tk-RRE vector may be assessed by monitoring its ability:
 (a) to completely inhibit or significantly decrease plasma viral rebound upon ART discontinuation.
 (b) to diminish SIV+ cells, including CD4 T cells and monocytes in the peripheral blood.
 (c) to significantly reduce cerebrospinal fluid (CSF) viral load.
 (d) to significantly reduce SIV+ macrophages/microgalia in the brain.
 (e) to significantly reduce SIV+ cells in lymphoid tissues and the gut.
 (f) to significantly reduce SIV lesions in the brain.

TABLE 2

Summary of assays used for the efficacy assessment

| | Efficacy Evaluation | Assays used for evaluation |
|---|---|---|
| (a) to completely inhibit or significantly decrease plasma viral rebound upon ART discontinuation | Reduction of plasma viral load & rebound | PCR quantification of viral RNA in plasma |
| (b) to diminish SIV+ cells, including CD4 T cells and monocytes in the peripheral blood. | Reduction of viral reservoirs in PBMC | PBMC sorting & PCR quantification of viral DNA; PBMC dilution & viral replication assay |
| (c) to significantly reduce cerebrospinal fluid (CSF) viral load. | Reduction of CSF viral load | PCR quantification of viral RNA in CSF |
| (d) to significantly reduce SIV+ macrophages/microgalia in the brain | Reduction of SIV+ macrophages in the brain | Immunohistochemistry & In situ hybridization of SIV proteins & DNA/RNA, brain tissues. |
| (e) to significantly reduce SIV+ cells in lymphoid tissues and the gut. | Reduction of SIV+ cells in other tissues | Immunohistochemistry & In situ hybridization of SIV proteins & DNA/RNA. Other tissues |
| (f) to significantly reduce SIV lesions in the brain. | Reduction of SIV lesions | Histopathological examination of brain tissues. |

(a) HSV1-tk vector-mediated reduction of plasma viral rebound upon ART discontinuation: Blood sampling (20 ml peripheral blood per drawing) of injected monkeys in all groups will be initiated two weeks following viral infection and will continue on a monthly basis until the end of the study. Plasma SIV RNA will be measured using a standard protocol that can detect as few as 50 copies of RNA/ml (135, 136). Briefly, viral RNA will be prepared from 500 µl of cell-free plasma using a Qiagen Viral RNA Kit, and then reverse-transcribed using MMLV-RT. Viral cDNA will further be PCR amplified and quantified using an SIV DNA standard as previously described (134, 136).

(b) HSV1-tk vector-mediated reduction of SIV+ cells in the peripheral blood: Previous studies have suggested that both blood memory CD4 T cells and monocytes in the peripheral blood may harbor transcriptionally active HIV (28, 137, 138). For measuring the reduction of active viral reservoirs in the peripheral blood, PBMC (50 ml) will be drawn every 2 months, and will be purified and sorted with flow cytometry based on CD14, CD163, and CD68 for cells of the monocytes/macrophage lineages. CD4 T cells will also be identified and sorted with CD3, CD4, CD28 and CD95 for naïve, and central memory (CD28+CD95+) and effect memory (CD28-CD95+) (139, 140). Sorted cells will also be directly lysed to extract total genomic DNA for standard real-time PCR amplification of SIV DNA and integrated copies of SIV DNA as described (141, 142). As a complementary approach, latent viruses will also be recovered from PBMC by a quantitative limiting-dilution culture assay described previously (24, 143).

(c) HSV1-tk vector-mediated reduction of cerebrospinal fluid (CSF) viral load: It has been shown that ART can systemically diminish viral load which leads to lower viral burden in CSF (35, 129). However, viral DNA persists and CNS inflammation continues in some macaques (35). We expect that the HSV1-tk vector can target SIV DNA+ cells, leading to decrease of viral load in CSF. CSF will be acquired from the cerebello-medullary cistern of anesthetized macaques at 2 months after the final termination of ART, and immediately before euthanasia. Viral RNA will be measured by standard real-time RT-PCR as described above (135, 136).

(d) HSV1-tk vector-mediated reduction of SIV+ macrophages/microgalia in the brain: At the end of the study, the treated monkeys and control animals will be euthanized. The reduction of SIV+ cells in the brain tissues will be measured by three different complementary approaches: 1) flow cytometry sorting and PCR (SIV-DNA), 2) fluorescence in situ hybridization (SIV-DNA/RNA), 3) immunohistochemistry tissue staining (SIV p24). The cellular identity of SIV+ cells will also be identified by co-staining with labeled antibodies, including CD14, CD163, CD68, and MAC387+ for cells of the monocytes/macrophage lineages (125, 130, 144-146). To measure SIV+ cells by flow cytometry, tissues will first be digested (147). Cells in suspension will be harvested, washed, and then sorted with flow cytometry. Genomic DNA will be extracted and measured by real-time PCR for SIV-DNA and integrated SIV-DNA as described above. The decrease of Viral DNA in tissue cells will also be confirmed by fluorescence in situ hybridization (148-150). For tissue immunohistochemistry staining, small pieces of tissues will be immediately fixed in fixation buffer (2% Formalin, 0.04% gluteraldehyde, 0.01% NP-40 in PBS) for 2 hours at 4° C., and then sliced and stained with SIV-Gag-specific antibody 55-2F12. Stained tissues will be washed and post-fixed for microscopic imaging.

(e) HSV1-tk vector-mediated reduction of SIV+ cells in lympoid tissues and the gut: Additional to the brain, a complete tissue collection at necropsy will include thymus, spleen, multiple lymph nodes, gut, lung, bone marrow, kidney, and liver (131, 133, 134). The reduction of SIV+ cells in these tissues will be similarly analyzed as above by the three approaches. The cellular identity o SIV+ cells will also be identified by co-staining with labeled antibodies listed above, including CD14, CD163, CD68 for cells of the monocytes/macrophage lineages; CD3, CD4, CXCR4, and CCR5 for CD4 T cells; CD28 and CD95 for the central memory and effect T cell subsets; Ki67, CD38, HLA-DA, and CD69 for active cells.

(f) HSV1-tk vector-mediated reduction of SIV lesions in the brain:

Histopathological examinations will be performed on H&E (Hematoxylin & Eosin)-stained sections from four regions of the brain (frontal, cortex, basal gaglia, hippocampus, and brainstem). We will examine for possible reduction of inflammation or neuropathogenesis/injury caused by SIV infection. The TNPRC has 4 clinical pathologists that routinely analyze and provide report of histologic findings from collected tissues. At the end of the study, possible clinical symptoms of disease progress towards AIDS will be monitored and documented, using a standard protocol we routinely performed at Tulane (131, 133, 134).

EXAMPLES

The below Examples are illustrative and non-limiting.

Example 1: Construction of Rev-Dependent GFP Vector

As shown in FIG. 2A, the Rev-dependent GFP vector was assembled by cotransfection of HEK293T cells with the GFP-expressing Rev-GFP-RRE-SA, a helper construct pCMVA8.2 (68), and a construct expressing the VSV-G envelope. The assembled particles were used to identify HIV(AD8)-infected human macrophages (MDM). As shown in FIG. 2B, at 24 hours post HIV infection, cells were super-infected with Rev-GFP-RRE-SA particles using a low m.o.i (5 ng p24 per million cells). After 5 days, the cells were fixed and stained for the presence of intracellular HIV p24. GFP was detected only in HIV p24-positive cells, but not p24-negative cells, demonstrating specificity and indicating that a single Rev-dependent GFP viral particle is capable of detecting the presence of HIV in macrophages (50).

The Rev-dependent vector can also effectively identify 80-90% of HIV+ cells using concentrated viruses (52, 53). As shown in FIG. 3, different dosages of the Rev-GFP-RRE-SA particles were used to super-infect an HIV-infected human T cell, CEM-SS. GFP was detected only in HIV-infected cells, but not in uninfected T cells, even with the highest dosage used, confirming the strict requirement for HIV to trigger reporter gene expression. When different dosages of the Rev-GFP-RRE-SA particles were used to super-infect HIV+ T cells, we observed a dosage-dependent increase in GFP+ cells. The curve that fits these data is a rectangular hyperbola, defining this as a saturable process, and it predicts that 80-90% of the HIV-infected cells can be targeted by the GFP reporter virus (50) (FIG. 3B).

The HIV Rev-dependent vector, Rev-GFP-RRE-SA (or pNL-GFP-RRE-SA) has been deposited into the NIH AIDS Research and Reference Reagent Program (Cat#11466), and is currently available for research use.

Example 2: Selective Expression of Therapeutic Genes in HIV-Infected Cells

Based on the data shown above in Example 1, it appeared that therapeutic genes can be selectively expressed in HIV-infected cells. We therefore inserted a series of therapeutic genes into the vector (FIG. 4). We cloned four different types of therapeutic genes: anthrolysin 0 (AlnO) from *Bacillus anthracis*; diphtheria toxin A chain (DT-A) from *Corynebacterium diphtheria*; an indigenous, pro-apoptotic human gene, TRAF6 (tumor necrosis factor receptor-associated factor 6) (69, 70); and herpes simplex 1 virus thymidine kinase gene (HSV1-tk). These therapeutic genes induce cell death by different mechanisms (51-53).

To effectively deliver these therapeutic genes into HIV-positive cells, we have also overcome multiple technical hurdles to generate toxin-resistant cell lines for the assembly of high-titer Rev-dependent particles. We have been successful in generating several toxin-resistant cell lines, such as the DT-A resistant 5H7 cells (52, 53), and used them to produce sufficient amounts of viral particles. We have also tested the ability of these assembled Rev-dependent particles to selectively kill HIV-positive T cells and macrophages. Results from these studies have been published in Young et al. (52) and Wang et al. (53). The Rev-dependent AlnO viral particle can selectively kill 98% of infected macrophages (reduced HIV positive macrophages from 12.2% to 0.27%) (52), demonstrating that these vectors are effective in diminishing HIV-positive cells. We have also constructed a non-integrating Rev-dependent vector to deliver TRAF6 as an episomal DNA to alleviate the potential risk of integration-mediated mutagenesis. The non-integrating TRAF6 particles eliminated 66% HIV-positive peripheral blood mononuclear cells. The results have also been reported in Wang et al. (53).

For in vivo delivery, to demonstrate the safety of the Rev-dependent vector, we identically infected healthy macrophages (no HIV) with highly concentrated Rev-AnlO-RRE-SA for two weeks, but did not detect non-specific killing of macrophages by Rev-AnlO-RRE-SA (only 1% apoptotic cells versus 2% apoptotic cells in an empty vector-treated control), as reported in (52), thereby demonstrating that non-specific killing of uninfected cells is minimal. As supplementary evidence, we similarly infected HIV-negative Jurkat T cells with Rev-AnlO-RRE-SA, and observed stable integration of the vector DNA for several months without the non-specific killing of the HIV-negative Jurkat cells. In contrast, in a HIV-positive J1.1 Jurkat cell, similar infection led to the killing of J.1.1 and the disappearance of the AnlO-vector DNA within 6 days (52). Similar results were also obtained using the Rev-dependent TRAF6 vector (53). When HIV-uninfected cells were identically treated with the TRAF6 particles, we observed a minimal increase (below 2%) in cell death after 7 days of cell culture (from 4.4% background dead cells to 6.2% dead cells in TRAF6). This is significantly lower than the 66% reduction in HIV-positive cells. Based on these results, we concluded that the Rev-dependent TRAF6 particles do not have the capacity to cause massive non-specific killing of healthy cells (53).

Example 3: Developing Rev-Dependent Vector in SIV Infection of Rhesus Macaques To validate the efficacy of the vector in vivo using the SIV/rhesus macaque model, we converted our HIV-based vectors into SIV-based vectors by incorporation of RRE, multiple splicing sites (D1, A6, D3, A7), and Loop A (W) from the SIVmac239 genome. SIV also encodes Rev, and the Rev function is well-conserved among HIV and SIV strains. It has been shown that SIV Rev is capable of inducing cytoplasmic expression of incompletely spliced mRNAs (71), and that the Rev proteins of HIV-1 and HIV-2 can also transactivate SIV gene expression (72).

The HSV1-tk gene and the human TRAF6 gene (identical to monkey TRAF6) wre also cloned into the SIV-based vector (FIG. 5). The selection of HSV1-tk is based on several advantages of the system: (1) superior safety profiles—the system has been studied for over 30 years, and has undergone multiple clinical trials with few side effects observed (73, 74); (2) capable of targeting post-mitotic cells—HIV/SIV-stimulated DNA synthesis and DNA repair activity (75, 76) can be utilized for HSV1-tk-mediated killing. A similar approach using HSV1-tk to kill terminally differentiated synovial lining cells has been applied in a rabbit inflammatory arthritis model (77). (3) high titer particles can be assembled—the lack of cytotoxicity of HSV1-tk in the absence of ganciclovir (GCV) has permitted the production of high titer lentiviral particles ($>10^{10}$ transduction units) (73, 74), which can greatly facilitate the animal study.

TRAF6 is an indigenous human gene, and it induces apoptosis only when over-expressed (69, 70). In addition, the present inventor's preliminary study has shown that over-expression of TRAF6 has minimal toxicity to HEK293T cells, although it is toxic to other cells. High-titer TRAF6 virus was assembled using HEK293T cells (53).

Example 4: In Vivo Animal Study

To conduct the proposed animal trial, it was necessary to first develop a protocol for large-scale production of lentiviral particles that were further concentrated 500- to 1,000-fold through anion exchange and size-exclusion columns (FIG. 6). These particles were first evaluated for toxicity in mice and rhesus macaques by intravenous_(i.v.) injection. As a preliminary study, concentrated SIV Rev-dependent viral particles were injected into 5 mice and 2 rhesus macaques for initial safety assessment, using the IACUC protocol approved by George Mason University and Tulane University, where the animals were housed (mice at GMU, monkeys at Tulane). All animals appeared healthy with no noticeable adverse effects. The two macaques were euthanized to collect tissues for toxicity examination. Multiple tissues were examined and there were no observed differences in multiple tissues between the injected animals and a normal control animal.

For the initial animal studies, macaques were divided into 4 groups (Groups A to D, two animals per group) (Table 3 and FIG. 7).

TABLE 3

SIV and vSIV-HSV1-tk-RRE injection and treatment scheme

| Group | SIV Infection | ART | vSIV-HSV1-tk-RRE | Post vector injection |
|---|---|---|---|---|
| A = SIV infection only | SIV | NO | NO | N/A |
| B = SIV + ART only | SIV (12 weeks) | 6 months | NO | N/A |
| C = SIV + ART + vSIV-HSV1-tk-RRE | SIV (12 weeks) | 6 months | YES | No ART |
| D = SIV + ART + vSIV-HSV1-tk-RRE + ART | SIV (12 weeks) | 6 months | YES | ART, 2 weeks off and then 3 months on |

For Group A, monkeys were infected with 100 TCID50 of SIVmac239 using the standard infection protocol (78, 79, 80), but received no treatment.

For Group B, animals were similarly infected with SIV, but were treated with ART for 11 months. ART was then terminated to allow viral rebound to occur.

For Group C, animals were infected, treated with ART for 1 months and then interrupted for two weeks for injection with 0.5-1 ml of concentrated vSIV-HSV1-tk-RRE vector. Following vector injection, ART was not resumed. This was to permit vector amplification and mobilization with active SIV replication.

For Group D, animals were treated and injected similarly to Group C, but ART was resumed for 3 months after vector injection. The scheduled ART interruption during lentiviral vector injection is needed for vSIV-HSV1-tk-RRE infection and vector spread in the body; these peak in 7-10 days (81). The resumption of ART will inhibit uncontrolled SIV spread.

After approximately 3 months of vector injection, ART was terminated, and ganciclovir was administered intravenously for two weeks at a dosage of 10 mg/kg/day to induce the death and decay of SIV+ cells for Groups C and D. Following ganciclovir administration, all treatments were terminated, and viral rebound was monitored.

In this experiment, before the vector injection in Groups C and D, CD8 T cells were also transiently depleted with an anti-CD8 antibody, cM-T807. A major rationale for CD8 depletion is to prevent possible rapid clearance of cells carrying the Rev-dependent vector. Additionally, with CD8 depletion, the disease progresses much more rapidly, and CNS disease is much more consistent (77% of animals) (82-84). This may provide a more robust model system to assess the effects of the vector on rapid viral rebound.

The experiment results are summarized in FIG. 8.

For animals in Group A, as expected, infected animals retained high viral loads without ART treatment.

For animals in Group B, as expected, ART treatment diminished viral loads that rebounded quickly following ART termination.

For animals in Group C, the injection of vSIV-HSV1-tk-RRE/ganciclovir failed to inhibit viral rebound following ART termination, suggesting that the vector alone is not capable of competing with uncontrolled SIV replication.

However, for animals in Group D, the administration of vSIV-HSV1-tk-RRE/ganciclovir did block viral rebound following ART termination. In particular, one of the two animals, KC50, had viral loads diminished to base-line with ganciclovir treatment. Following the termination of ganciclovir, SIV viral rebound occurred again in KC50. We subsequently injected the animal with the second vector, vSIV-TRAF6(R)-RRE, which also diminished viral rebound. Following the first vSIV-TRAF6(R)-RRE injection, we performed a second batch injection of vSIV-TRAF6(R)-RRE four months later. This last injection occurred on Aug. 21, 2017, and this injection further diminished viral loads to the threshold of detection. All treatment was terminated after this injection.

Currently, KC50 has been self-controlling viral rebound, and stably maintaining a viral load to the undetectable level.

For the second animal, JT43, in Group D, we observed a similar pattern of delayed viral rebound, although viral rebounds were higher than in KC50. JT43 was euthanized in the summer of 2017, before the second batch vSIV-TRAF6(R)-RRE injections.

We further quantified viral loads in CSF (cerebrospinal fluid) and found that KC50 has been stably maintaining undetectable viral load.

The results from our proof-of-concept animal study (FIG. 8 and FIG. 9) provide the first experimental evidence that the Rev-based vectors have the great potential to diminish viral rebound in vivo and may eventually lead to a cure or functional cure.

Importantly, the long-term viral remission in KC50, both in the peripheral blood and in CSF, is remarkable and unprecedented, given that the animal is infected with the most pathogenic SIVmac239, and is also negative for MamuA*01, B*08 and B*17 expression.

Example 5: Empty Rev-Dependent Vector can Inhibit HIV Replication and Reduce Viral Loads and Rebound As demonstrated above in the animal study data of Example 4, the present inventor made the unexpected discovery that the Rev-dependent vector itself can also reduce viral loads and rebound even without the expression of a functional gene. In other words, an empty Rev-dependent vector can inhibit HIV replication and reduce viral loads and rebound. This was neither known nor expected before the present animal trial.

As explained above, empty vector refers to a Rev-dependent vector that contains LTR and RRE but does not contain a therapeutic gene, such as TRAF6, for targeting $SIV^+$ cells, yet still can decrease viral rebound in vivo. This is so for a number of reasons, including:

1) Competitive inhibition of HIV transcription, splicing, and nuclear export: The Rev-dependent vector contains both LTR and RRE. Once inside HIV+ cells, the Rev-dependent vector can compete for the binding of cellular factors and HIV Tat to the LTR, and Rev to the RRE. Thus, the vector can inhibit HIV transcription, splicing, and viral RNA nuclear export.

2) Competitive inhibition of HIV genome packaging: The Rev-dependent vector also contains a functional genome packaging signal. Once inside an HIV+ cells, the Rev-dependent vector can compete for cellular and viral proteins involved in viral genome packaging. In the presence of the Rev-dependent vector, HIV-infected cells will release defective virion particles.

3) Protection of uninfected cells from being infected: The Rev-dependent vector can be delivered into healthy, HIV-uninfected cells. If a cell carryies the Rev-dependent vector, the cell can be rendered to become partial or completely resistant to HIV infection.

4) Stimulation of anti-HIV immunity: The Rev-dependent vector virion particles have identical structure as HIV particles. When the Rev-dependent particles are injected into the body, they will stimulate anti-HIV immunity, similar to an attenuated vaccine particles.

Thus, from the animal data presented in Example 4, the present application provides methodology for reducing SIV/HIV viral rebound and inactivating viral reservoirs in a subject, comprising administering to the subject a composition comprising a Rev-dependent vector expressing a gene or expressing no genes. The vector can inactivate viral reservoirs through competitive inhibition of HIV transcription and viral genome packaging.

What is claimed is:

1. A method for killing of HIV+positive cells to a subject in need thereof, comprising:
    (a) administering an antibody or anti-HIV/SIV drug to deplete CD8 T cells from the subject's body to ensure no rejection of a therapeutic vaccine by the body's killer T cells (CD8);
    (b) injecting a HIV vaccine particle comprising a Rev-dependent vector system for selective killing of HIV-infected cells;
    (c) ceasing anti-HIV therapy with combination antiretroviral therapy (cART) during vaccine particle injection for a period sufficient to allow the injected vaccine particles to amplify and replicate; and
    (d) following vaccine particle amplification, reinitiating anti-HIV therapy with combination antiretroviral therapy (cART) to decrease viral load to a base line.

2. The method of claim 1, wherein the period sufficient is 1 to 20 days.

3. A method of decreasing viral rebound, comprising:
    administering to a human patient in need of treatment for HIV-1 a regimen of highly active antiretroviral therapy (HAART) for a period of time sufficient to reduce plasma viremia in the human patient;
    thereafter suppressing the regimen and during the suppression period administering a rev-dependent lentiviral vector so as to allow sufficient replication of rev-dependent lentiviral in the HIV-1 infected cells; and
    thereafter administering the human patient a second regimen of HAART.

4. The method of claim 3, wherein the time sufficient to reduce plasma viremia of HIV-1 in the human patient to less than 5%.

5. The method of claim 1, further comprising administering a cytokine; a HDAC inhibitor; a chemotherapy drug; a hybrid CD4-toxin that binds to the viral envelope; or an HIV LTR-based lentiviral vector capable of expressing HSV1-tk.

6. The method of claim 3, wherein the regimen includes administering one or more antivirals chosen from Tenofovir, Emtriva, and Norvir.

7. The method of claim 5, wherein the cytokine is chosen from IL-2 and INF-γ; the HDAC inhibitors are chosen from valproic acid and vorinostat; and the chemotherapy drug is fludarabine.

\* \* \* \* \*